United States Patent [19]

Putnam

[11] Patent Number: 5,079,007
[45] Date of Patent: Jan. 7, 1992

[54] CONTROLLED RELEASE OF ANTIBIOTIC SALTS FROM AN IMPLANT

[75] Inventor: Michael L. Putnam, Mattawan, Mich.

[73] Assignee: The Upjohn Company, Kalamazoo, Mich.

[21] Appl. No.: 459,723
[22] PCT Filed: Jul. 1, 1988
[86] PCT No.: PCT/US88/02180
§ 371 Date: Jan. 16, 1990
§ 102(e) Date: Jan. 16, 1990

Related U.S. Application Data

[63] Continuation of Ser. No. 79,188, Jul. 29, 1987, abandoned.

[51] Int. Cl.$^5$ ............................................. A61K 31/545
[52] U.S. Cl. .................................... 424/422; 424/426
[58] Field of Search ................... 424/422, 426, 468; 514/186, 200, 202, 206, 207, 210; 540/227

[56] References Cited

U.S. PATENT DOCUMENTS 4,443,428 4/1984 Oshlack et al. ................. 424/468
4,877,782 10/1989 Cazers et al. .................... 514/186
4,902,683 2/1990 Amin et al. ...................... 514/206

Primary Examiner—Thurman K. Page
Assistant Examiner—Amy Hulina
Attorney, Agent, or Firm—Sidney B. Williams, Jr.

[57] ABSTRACT

An controlled release implant antibiotic formulation comprising (a) a crystalline salt of the antibiotic; (b) an amorphous salt of the antibiotic; and (c) excipients; whereas the excipients comprise from 0% to 10% of the tablet by weight. A particularly effective formulation provided is made from the antibiotic ceftiofur which has the formula

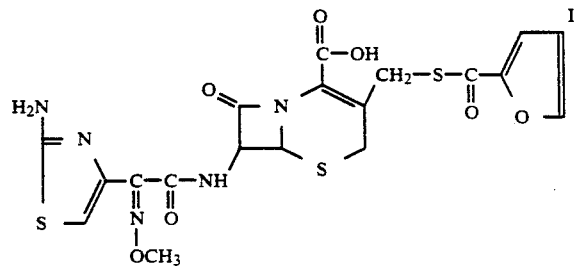

5 Claims, No Drawings

CONTROLLED RELEASE OF ANTIBIOTIC SALTS FROM AN IMPLANT

This is a continuation of U.S. application Ser. No. 07/079,188, filed July 29, 1987, now abandoned.

FIELD OF THE INVENTION

The present invention relates to the controlled release of antibiotics.

BACKGROUND OF THE INVENTION

It is known in the pharmaceutical art to prepare compositions which provide for slow release of pharmacologically-active substances contained in said compositions after oral administration to humans and animals. Such slow-release compositions are used to delay absorption of a medicament until it has reached certain portions of the alimentary tract. Such controlled release of a medicament in the alimentary tract further maintains a desired concentration of said medicament in the blood stream for a longer duration than would occur if conventional rapid release dosage forms are administered.

A controlled-release formulation comprising a matrix having dispersed therein both the pharmacologically-active salt form of a medicament and the free base form of the same medicament is described in U.S. Pat. No. 4,443,428. In each of the formulations described therein, the amount of excipients is in excess of 20% by weight. A similar formulation, but one that is based upon varying the water solubility of the active medicament, is described in WO-A-8102975.

Controlled-release formulations containing mixed esters of a medicament are described in FR-A-2571371.

Derwent abstracts a European patent application where a mixture of crystalline diasteromeric salts of a medicament causes production of isomers to produce a sustained release effect.

Ceftiofur (Formula I) is a known cephalosporin antibiotic, and is disclosed in U.S. Pat. No. 4,464,367.

SUMMARY OF THE INVENTION

The present invention particularly provides a formulation providing for the controlled release implant of a cephalosporin antibiotic, consisting of (a) a crystalline salt of the cephalosporin; (b) an amorphous salt of the cephalosporin; and (c) excipients; wherein the excipients comprise from 0% to 10% of the formulation, e.g. a tablet, by weight.

DESCRIPTION OF THE INVENTION

Intramuscular implantation is the preferred route of administration of the formulation.

The amount of crystalline salt can vary from 20% to 90%, preferably 80% to 90%, by weight. Crystalline salts that can be used include the hydrohalide salts, e.g. ceftiofur hydrochloride (preferred), ceftiofur hydrobromide and ceftiofur hydroiodide. In addition to the sodium salt, other alkali metal salts that can be used are the potassium and lithium salts, i.e., ceftiofur sodium salt, ceftiofur potassium salt and ceftiofur lithium salt.

The crystalline and amorphous salts can be blended and compressed with or without additional excipients to yield an implant with controlled-release characteristics.

A particularly effective formulation can be prepared utilizing ceftiofur monohydrochloride as the crystalline salt and the corresponding sodium salt, hydrate (ceftiofur sodium salt) as the amorphous salt.

Pellets of the formulations of this invention can be made by mixing the crystalline and amorphous salts and compressing them under standard press conditions.

Particularly effective formulations contain no excipients. Alternatively, excipients such as high molecular weight polyethylene glycols or polyvinyl pyrrolidone, up to 4% of total weight, as excipients, can be added to the formulation. Also, a lubricant and stabilizer such as stearic acid may be added. However, the weight of excipients should not exceed 10% and preferably 7% of the total tablet weight.

DESCRIPTION OF THE PREFERRED EMBODIMENT

The present invention is seen more fully by the example given below.

EXAMPLE

A powder mixture suitable for compression can readily be made by blending the proper weight to weight ratio (for example, 50/50) of crystalline ceftiofur hydrochloride and amorphous ceftiofur sodium salt in a glass mortar using appropriate mixing techniques. Portions of the mixture can be weighed and compressed using a standard laboratory Carver press and tablet tooling capable of containing the entire sample, e.g. 20.6 mm (13/16 inch) tablet tooling. Compression of up to 8.9 kN (2000 pounds) should be sufficient to generate an acceptable tablet. Painting the product contact surfaces of the tooling with a magnesium stearate/ethanol suspension will alleviate any problems with the compressed form sticking in the die.

The dissolution media should be made with normal care. While any buffered medium should work, at pH 7.4, Sorenson's buffer was used in this case. The solution was filtered under vacuum through a 4.5 $\mu$m filter to remove particulates and deoxygenate the liquid. After filtration, the buffer should be used within eight hours to prevent effects from the reincorporation of oxygen.

A USP dissolution testing apparatus with paddles was used in this case. Paddle rotation was restricted to 50 rpm. The kettles were filled with 900 ml of the filtered buffer solution. Sampling was continuously performed by using a multi-channel, diastolic pump connected to a UV/VIS with six flow cells. The pump moved the liquid through the flow cells at 60 ml/minute. Each flow cell was monitored once every minute and the absorbance value at 332 nm was recorded.

The absorbance from freshly-prepared standard solutions of both salt forms was recorded after each run. The concentrations selected exceeded the range anticipated from the complete dissolution of a given table in the 900 ml of buffer. Linear Least Squares fitting was performed on each standard curve set and used in extrapolating concentration values from the absorbance data.

Results for formulations containing different ratios of crystalline salt ("HCl") to amorphous salt ("Na") are tabulated below. Total Dissolution Time is an approximation based on observation and absorption data. All results are the average of those for six 600 mg tablets.

| Percent HCl/Na | Average Time (min) for 50% Dissolution | Average Time (min) for Total Dissolution |
| --- | --- | --- |
| 0/100 | 6 | 20 |
| 20/80 | 10 | 45 |
| 40/60 | 23 | 90 |
| 60/40 | 34 | 140 |
| 80/20 | 53 | 175 |
| 100/0 | 66 | 400* |

*Estimated from partial data

FORMULA

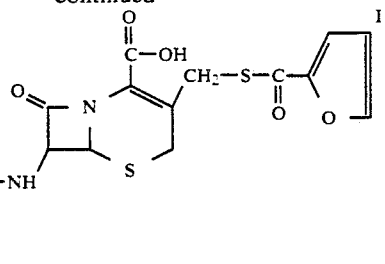

I claim:

1. A controlled release implant cephalosporin formulation consisting of (a) a crystalline salt of cephalosporin in the amount of about 20% to about 90% by weight; (b) an amorphous salt of cephalosporin; and (c) excipients; wherein the excipients comprise from 0% to 10% of the formulation by weight.

2. A formulation according to claim 1 wherein the excipients comprise from about 0% to about 7% of the implant by weight.

3. A formulation according to claim 1 or claim 2, wherein the cephalosporin is ceftiofur.

4. A formulation according to claim 3, wherein the crystalline salt is ceftiofur hydrochloride and the amorphous salt is sodium ceftiofur.

5. A formulation according to claim 4, which comprises about 80% to about 90% by weight of the ceftiofur hydrochloride.

* * * * *